(12) United States Patent
O'Connell

(10) Patent No.: US 7,190,449 B2
(45) Date of Patent: Mar. 13, 2007

(54) CELL TRAY

(75) Inventor: Daniel G. O'Connell, Kihei, HI (US)

(73) Assignee: Nanopoint, Inc.

( * ) Notice: Subject to any disclaimer, the term of this patent is extended or adjusted under 35 U.S.C. 154(b) by 449 days.

(21) Appl. No.: 10/693,953

(22) Filed: Oct. 28, 2003

(65) Prior Publication Data

US 2006/0119843 A1   Jun. 8, 2006

Related U.S. Application Data

(60) Provisional application No. 60/421,566, filed on Oct. 28, 2002.

(51) Int. Cl.
*G01N 1/10* (2006.01)

(52) U.S. Cl. ..................... 356/246; 356/326

(58) Field of Classification Search ............ 356/244, 356/246, 326
See application file for complete search history.

(56) References Cited

U.S. PATENT DOCUMENTS

| | | | |
|---|---|---|---|
| 4,415,405 A * | 11/1983 | Ruddle et al. ............ 356/244 |
| 5,004,307 A | 4/1991 | Kino et al. | |
| 6,208,886 B1 | 3/2001 | Alfano et al. | |
| 6,238,911 B1 * | 5/2001 | Kasahara ............ 356/246 |
| 6,519,032 B1 * | 2/2003 | Kuebler et al. ......... 356/246 |
| 6,818,907 B2 | 11/2004 | Stark | |
| 2002/0173033 A1 * | 11/2002 | Hammerick et al. ..... 435/305.2 |
| 2003/0020915 A1 * | 1/2003 | Schueller et al. ......... 356/246 |
| 2003/0215844 A1 | 11/2003 | Chapsky et al. | |
| 2005/0047971 A1 * | 3/2005 | Clements et al. ........... 422/102 |

OTHER PUBLICATIONS

Milster et al.; *Super-Resolution by Combination of a Solid Immersion Lens and Aperture*; The Japanese Society of Applied Physics, Part 1, No. 3B; Mar. 2001.

Hecht et al.; *scanning near-field optical microscopy with aperture probes: Fundamentals and applications*; Special Topic: Near-field Microscopy and Spectroscopy; Journal of Chemical Physics; vol. 112, No. 18; May 8, 2000.

(Continued)

*Primary Examiner*—Gregory J. Toatley, Jr.
*Assistant Examiner*—Kara Geisel
(74) *Attorney, Agent, or Firm*—James Creighton Wray

(57) ABSTRACT

A cell tray has a multi-dimensional array of cells in precise, equally spaced wells (cubicles or silos) containing medium of interest. The ordered cell array enables automated processing as well as simultaneous monitoring and analyzing of a large matrix of cells, biological fluids, chemicals and/or solid samples. The invention is an integrated device and is fabricated into substrates similar to microscope slides. The ordered array of cells in precise locations helps in parallel analysis and processing of cells simultaneously. Each cell cubicle or silo in the array is located equidistant from its nearest neighbors in an orthogonal direction. The location of each well can be precisely measured and recorded in an automated processing system. Included in the bottom of each cell well is an optional micro-lens. An array of probes provides parallel cell processing and monitoring capabilities, including microinjection and microscope analysis. The cell tray when integrated with the Precision Optical Intracellular Near Field Imaging/Spectroscopy Technology (POINT or NANOPOINT) device results in sub-wavelength high-resolution imaging with a nanosensor array capable of imaging inner regions of living cells without destroying its natural environment.

75 Claims, 6 Drawing Sheets

OTHER PUBLICATIONS

Betzig & Chichester; *Single Molecules Obseerved by Near-field Scannning Optical Microscopy*; Science, New Series; vol. 262, No. 5138; Nov. 26, 1993; pp. 1422-1425.

Mansfield & Kino; *Solid Immersion Microscope*; Appl. Physics Letter; vol. 57, No. 24; Dec. 10, 1990.

D. V. Palanker et al.; *On contrast parameters and topographic artifacts in near-field infrared microscopy*; Journal of Applied Physics, vol. 88, No. 11; Dec. 1, 2000.

Tom D. Milster et al.; *The Nature of the Coupling field in Optical Data Storage using Solid Immersion Lenses*; The Japanese Society of Applied Physics, Part 1, No. 3B: Mar. 1999.

Jonathan D. Bui et al.; *Probing intracellular dynamics in living cells with near-field optics*; Journal of Neuroscience Methods 89 (1999) 9-15; Feb. 27, 1999.

Tang et al.; *Consideration and control of writing conditions with a near-field APSIL probe*; Proceedings of International Symposium on Optical Memory and Optical Data Storage/2002; ISBN 0-7803-7379-0; Published:2002; pp. 243-245.

* cited by examiner

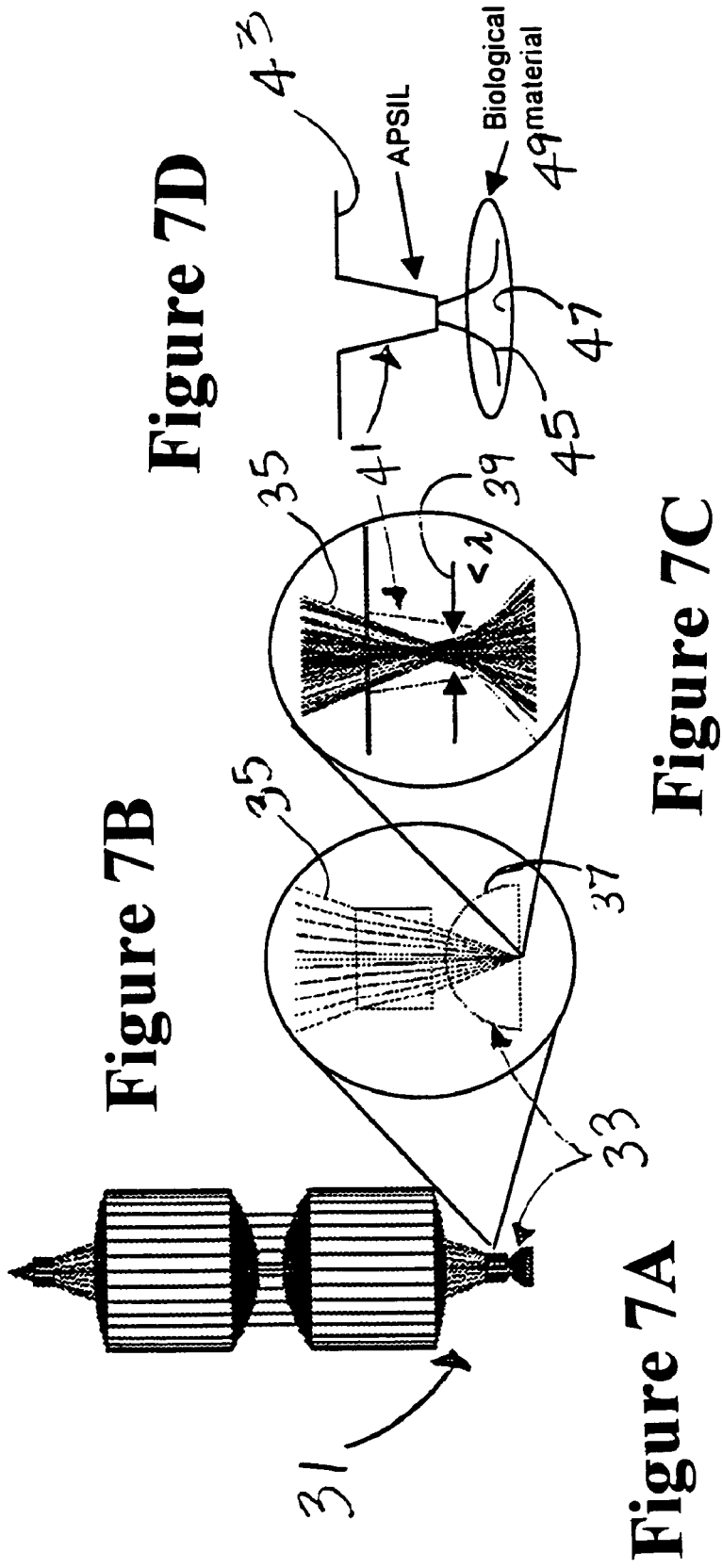
Figure Solid Immersion Lens with Near-field Aperture (APSIL). (a) SIL Microscope configuration. (b) enlarged view of SIL. (c) enlarged view of near-field aperture probe. (d) Near-field illumination of cell.

(a) Oceanit's "Cell Tray" to hold individual cells stationary in a precise array (b) Near-Field probe technique using probe at the base of a SIL (c) diagram of multiple probes fabricated in combination with a cell well array

CELL TRAY

This application claims the benefit of U.S. Provisional Application No. 60/421,566, filed Oct. 28, 2002.

BACKGROUND OF THE INVENTION

Current methods of cell analysis involve living cells cultured in petri dishes, well plates and on microscope slides. These previous methods of culturing live cells suffer from inconsistent arrangement of cells and slow processing times. The arrangement of the cells in previous cell analysis methods is random, with areas of high cell congregation and other regions where cells are sparsely distributed.

Biological research laboratories and biological instrument and supply companies are constantly looking for new methods to make cell analysis more efficient.

Needs exist for improved simultaneous multiple cell analysis, observation and cell injections.

SUMMARY OF THE INVENTION

The present invention preferably has a two-dimensional array of cells in precise, equally spaced rectangular cubicles or cylindrical silos (otherwise referred to individual cell wells) that contain life support medium. The ordered cell array enables automated processing as well as simultaneous monitoring and analyzing of a large matrix of cells, biological fluids, chemicals and/or solid samples. The present invention is an integrated device and is fabricated into substrates similar to microscope slides used for conventional microscope viewing or spectroscopic studies.

The present invention provides a method of containing an ordered array of cells in precise locations for use in parallel analysis and processing of cells simultaneously. Each cell well, in the square array, is located equidistant from its nearest neighbors in an orthogonal direction. The location of each well can be precisely measured and recorded in an automated processing system. Included in the bottom of each cell well are micro-optic lenslets or micro-machined diffractive optic lenses as an optional feature to provide additional resolution when combined with conventional microscope or to enhance the POINT microscope, or other instrumentation. An array of probes provides parallel cell processing and monitoring capabilities, including microinjection and microscope analysis.

The present invention works well with the Precision Optical Intracellular Near Field Imaging/Spectroscopy Technology (POINT or NANOPOINT) invention described in co-pending patent application Ser. No. 10/290,528 which is incorporated herein by reference in its entirety.

POINT is a novel high-resolution instrument for analyzing and comparing molecular characteristics of cells. Currently, confocal microscopes, MRI and ultrasound cannot image to a 50 nm resolution and the use of electron microscopes destroys the cells. The POINT system is a nanosensor array capable of imaging inner regions of living cells without destroying its natural environment. The system uniquely provides new information about the molecular makeup of a cell.

The POINT system is not limited to just imaging inside living cells but it is also useful for any application where sub-wavelength resolution is important. Another application of the POINT system is to observe gene expression in cells.

POINT is a near-field microscope imaging system that converts any conventional microscope to have near-field capability. The POINT microscope stage may be installed on most conventional microscopes and may also be transported between microscopes. The new microscope stage has specialized controllers to maneuver the solid immersion lens or fiber-optic probe and control the distance to the sample to sub-wavelength proximity.

This new microscope houses either an array of fiber probes or a solid immersion lens, which accepts a high numerical aperture beam from a high NA objective within a conventional microscope. The solid immersion lens reduces the wavelength in the glass thereby forming a smaller light spot at its internal focus. POINT combines a multiple aperture near-field probe array with the cell tray enabling multiple live cell processing with sub-wavelength resolution imagery and spectroscopy.

The POINT microscope is suitable for imaging living biological samples using a technique that accommodates large-scale production. The POINT near-field microscope platform may be interfaced with most conventional laboratory light microscopes thus making near-field available to a vast research community.

The POINT system may be applied to near field optical microscopy applications as a research tool for medical and biological imaging as well as medical diagnostics as an early warning device for detection of diseased cells and to aid in drug development and treatments. POINT technology can be used to transform an existing microscope into a high resolution nanoscope.

In addition to use in analysis and processing of living cells, the present invention is also useful in analysis and processing of other fluid or solid samples.

These and further and other objects and features of the invention are apparent in the disclosure, which includes the above and ongoing written specification, with the claims and the drawings.

BRIEF DESCRIPTION OF THE DRAWINGS

FIG. 7A shows an solid immersion lens (SIL) microscope configuration.

FIG. 7B is an enlarged view of a solid immersion lens.

FIG. 7C is an enlarged view of the near-field aperture probe.

FIG. 7D is a near-field illumination of a cell.

DETAILED DESCRIPTION OF THE PREFERRED EMBODIMENTS

The present invention provides a method of containing an ordered array of cells 1 in precise locations for use in parallel analysis and processing of cells 5 simultaneously.

Figure 1:
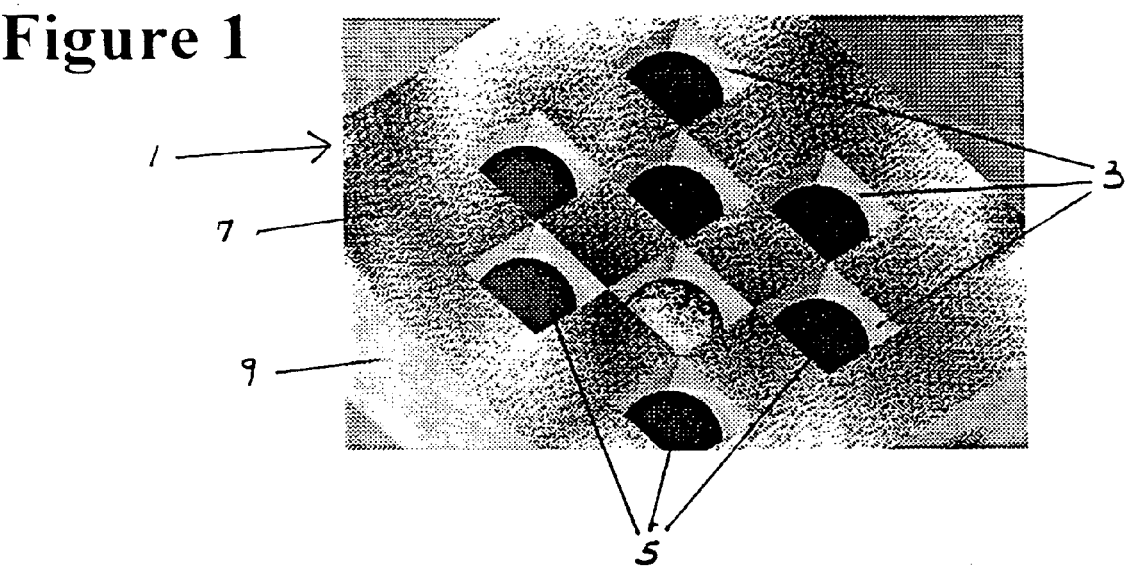
FIG. 1 is a schematic of the cell tray.

As shown in FIG. 1, each cell cubicle or silo 3, in the square cell array 1, is located equidistant from its nearest neighbors in an orthogonal direction.

The cell tray 1 is fabricated using micro-machining techniques. A layer of chrome is deposited onto the cell carrier substrate 9. A layer of photoresist 7 is spin coated over the chrome. The material for the cell carrier substrate 9 includes, but is not limited to, fused silica (quartz), soda-lime glass, silicon, germanium, sapphire, and plastic. Other base substrates are used depending on the desired optimal transmission properties in various parts of the electromagnetic spectrum.

A lithographic mask is designed on computer and directly written on the photoresist with a laser scanning microscope. Alternatively a two-axis Ronchi ruling is used to expose a crossed-grating pattern on the photoresist layer 7. Alternatively a lithographic shadow mask may be substituted for the Ronchi grating. The shadow mask consists of a two-dimensional array of square or circular apertures to optimize performance in different applications. A holographic exposure process may also be used to generate a crossed-grating interference pattern in the photoresist.

The photoresist 7 is exposed using laser light or broadband white light. Regions in the photoresist 7 that were in shadow and not exposed remain as surface structure in the photoresist after the developing process (the opposite structure would result from negative photoresist). A two-dimensional ordered array of square, circular or other geometric shaped regions is removed during a developing process.

The fabrication process is not limited to negative or positive photoresist 7 processes. A positive photoresist 7 can be substituted along with a negative of the aperture mask. In addition the cell cubicles or silos 3 can be fabricated using e-beam or deep UV lithography in PMMA substrate or any other optical substrate. The substrate 9 may be any material chosen based on its optical and mechanical properties including, but not limited to, soda lime glass, borosilicate glass, Fused Silica, PMMA, Sapphire, Silicon or Germanium. The cell containment features including fluid channels and micro-optic lenses can be produced using hot press, embossing or stamping on suitable glass or plastic substrates.

The exposed chrome regions are removed with a liquid chemical etch. The remaining photoresist can then be removed resulting in a metallic mask outline of the desired pattern. The substrate 9 are processed using a reactive ion etching procedure. The etch process results in features etched or transferred into the cell tray base substrate 9 without affecting the chrome layer.

Figure 2:
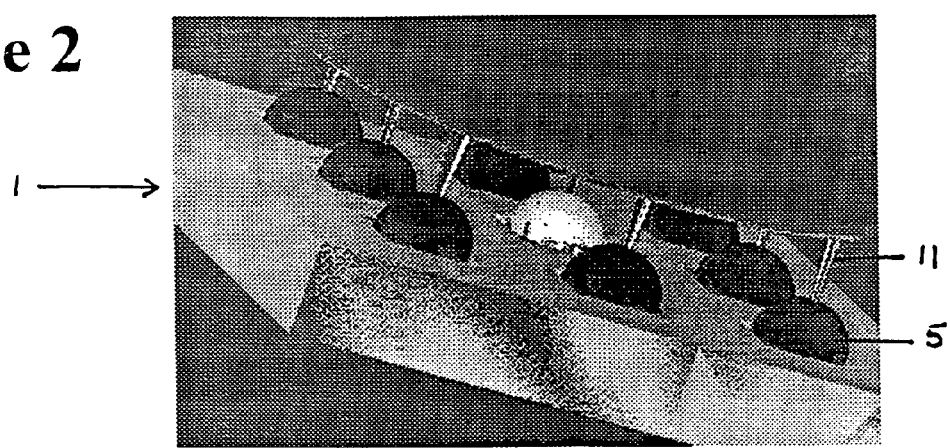
FIG. 2 is a diagram of the cell tray with a probe array.

As shown in FIG. 2, the cell tray 1 can be used for parallel processing and analysis of cells simultaneously, using an array of probes 11 that are fabricated with spacing identical to the cell cubicles 3. The present invention provides added capability for parallel cell processing and monitoring, including microinjection and microscope analysis.

Figure 3:
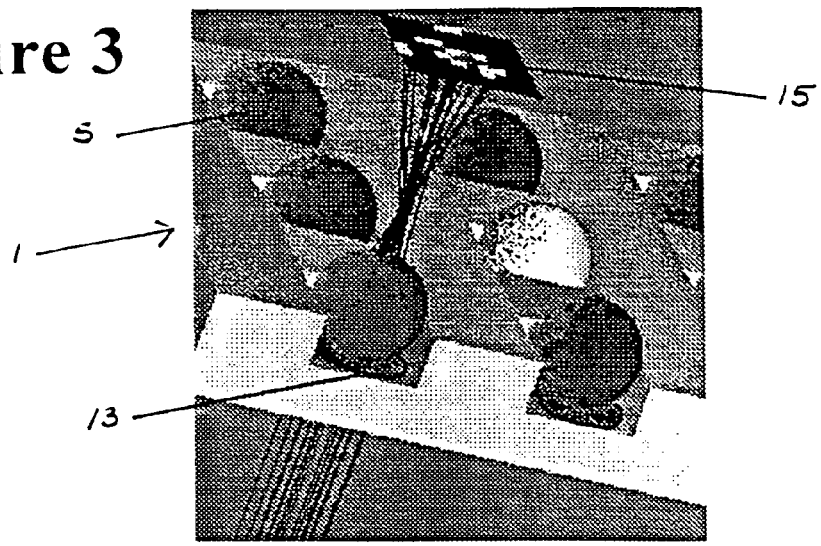
FIG. 3 is a diagram of the cell tray integrated with a microscope objective lens array.

Referring to FIG. 3, the cell tray 1 incorporates an optional micro-optical lens element 13 situated at the base of each cell cubicle 3. The micro-lens 13 provides microscopic imaging and analysis, for example using solid and liquid immersion optical techniques for high-resolution imaging.

The micro-optic lens (diffractive, refractive or holographic) lens 13 is produced as an integrated part of the cell tray 1 during the same micro-machining (or embossing, stamping or pressing) process that generates the cell cubicles 3. For example a Fresnel type lens structure 13 is produced at the base of the well 3, with a binary transmittance or grayscale mask, as well as a phase mask or kinoform. The cell tray 1 may be integrated with a microscope objective lens array 15 above the sample cell 5.

Figure 4:
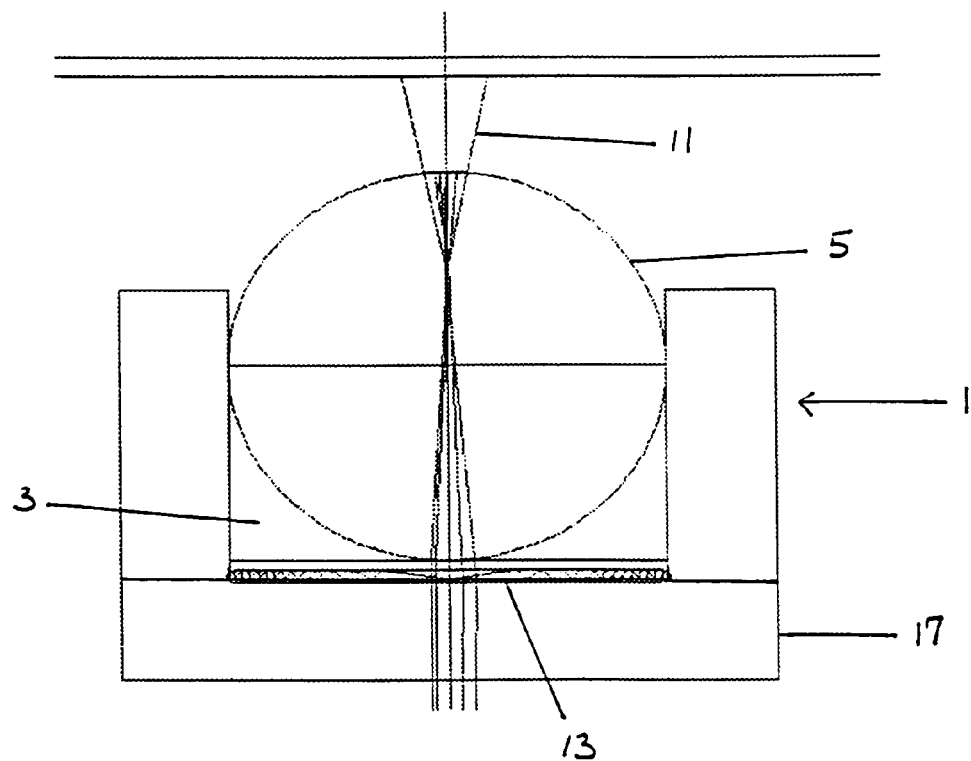
FIG. 4 is a schematic of the cell tray with a cell probe and Fresnel lens.

As shown in FIG. 4, a two-dimensional array 1 of cubicles or silos 3 are machined into an optical or other substrate 9 for multiple cell analysis, or the analysis of fluid or solid samples simultaneously. The cell tray 1 can be mounted onto an invar backing plate 17, with a clear aperture for viewing transmission. The invar 17 or another material is used as mechanical support to maintain a uniform flat surface of the cell tray 1.

This may be beneficial when the CellTray is fabricated in a thin glass wafer similar in dimensions to a microscope cover slip.

The cell tray 1 may contain any number of cell cubicles 3 in a linear array or precisely determined two-dimensional array 1 and is limited only by the size of the substrate 9 and the ion beam in the reactive ion etching camber. The lateral dimensions of the cubicles and depth can vary between cell tray devices and is not limited to a single fixed dimension.

The precise arrangement of the cell wells 3 enables multiple cell analysis and processing simultaneously, which is currently not possible. This invention increases the speed of cell analysis, as well as provides new techniques for monitoring cell and other samples under a variety of conditions.

Figure 5:
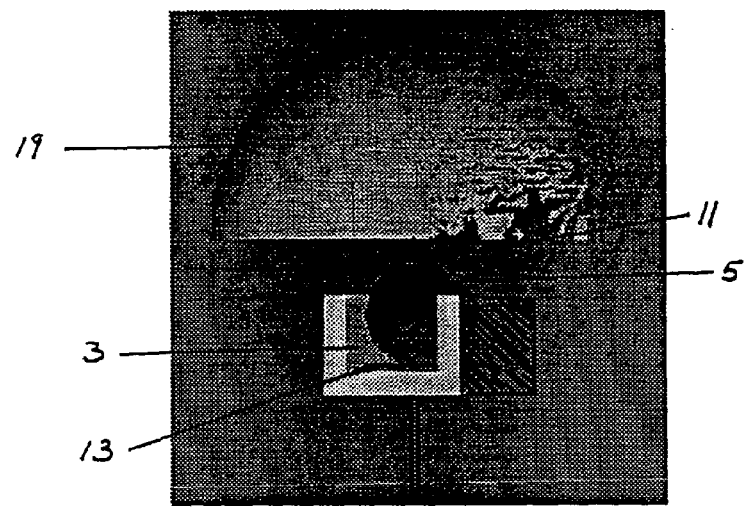
FIG. 5 is view of the cell tray interfacing with the automated system for cell monitoring.

As shown in FIG. 5, each cell well 3 is indexed by an automation system 19 for cell monitoring and processing. The array of cell cubicles 3 provides for the simultaneous collection of light for imaging, and spectroscopy of samples in multiple regions of the spectrum.

The cell tray 1 of the present invention is machined into conventional microscope slides or cover slips, as well as other optical substrates. The cell tray system 1 is used in both transmission or reflection mode microscopes and spectrometer configurations in the ultraviolet, visible and infrared regions of the electromagnetic spectrum.

Figure 6:
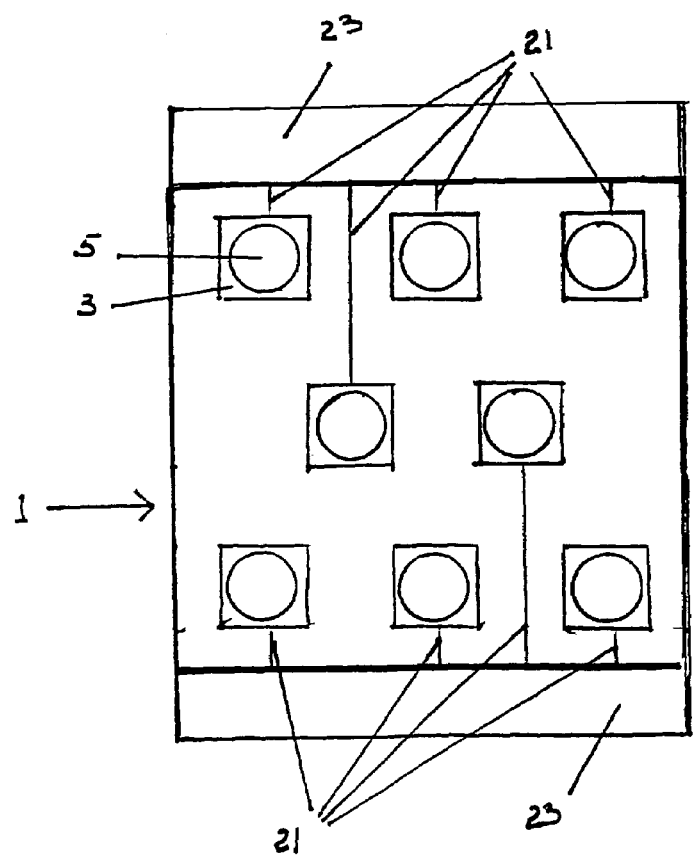
FIG. 6 is a top view of the cell tray with a fluid delivery system and fluid channels.

As shown in FIG. 6, an integrated network of microchannels 21 can be etched into the substrate 9 to provide fluid delivery to each cell well 3. Similar to forming wire traces in an integrated circuit, a network of fluid channels 21 can be etched into the substrate 9 using photolithography transfer process or shadow mask. Each cell well 3 has a dedicated fluid delivery channel 21 that extends from the cell well 3 to the edge of the optical substrate 9 or wafer and attached to a fluid delivery manifold 23. This allows different drug agents, chemicals of different concentration or pH, dyes or any liquid to be delivered via a fluid channel 21 to each cell well 3. This integrated micro-optic chip on an optical wafer enables parallel processing and analysis of a large number of cells as well as precise and regulated drug delivery or other fluid delivery processes. The present invention also enables the rapid analysis of a large number of living cells for various experiments in cancer and other disease research and drug development. The present invention enables flow analysis of live cells with canals that are wide channels that run across the length or width of the cell tray. These canals enable live cells to flow across the wafer to enable cell counting, cell size measurement and other live cell parameters.

FIGS. 7A–7D show a solid immersion lens with near-field aperture. FIG. 7A is a microscope/SIL combination 31. FIG. 7B is an enlarged view of the SIL 33, illustrating the incoming rays 35 normal to the convex side 37 of the SIL 33. FIG. 7C is an enlarged view of the near-field aperture probe 41. A computer model shows light rays 35 focusing halfway 39 through the near-field probe 41 placed at the base 43 of the SIL 33. FIG. 7D shows the near-field illumination 45 of a cell 47 in biological material 49.

Figure 8A:
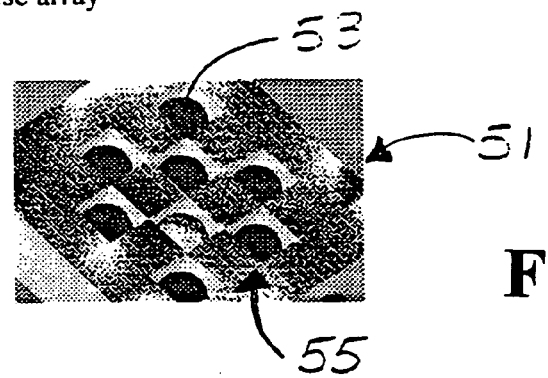
FIG. 8A shows the "Cell Tray" holding individual cells stationary in a precise array.
Figure 8B:
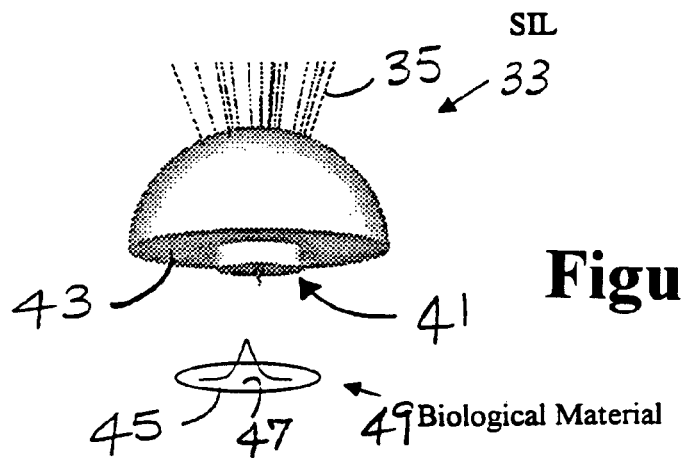
FIG. 8B shows a near-field probe technique using the probe at the base of an SIL.
Figure 8C:
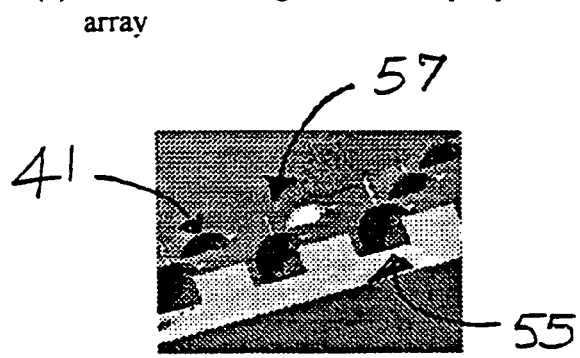
FIG. 8C is a diagram of multiple probes fabricated in combination with a cell well array.

FIG. 8A shows cell tray 51. The cell tray is a cell containment system 51 for holding individual cells 53 stationary in a precise array 55. FIG. 8B shows a near-field probe technique using the probe 41 at the base 43 of the SIL 33. FIG. 8C is a diagram of multiple probes 41 fabricated in combination with a cell well array 55.

Figure 9:
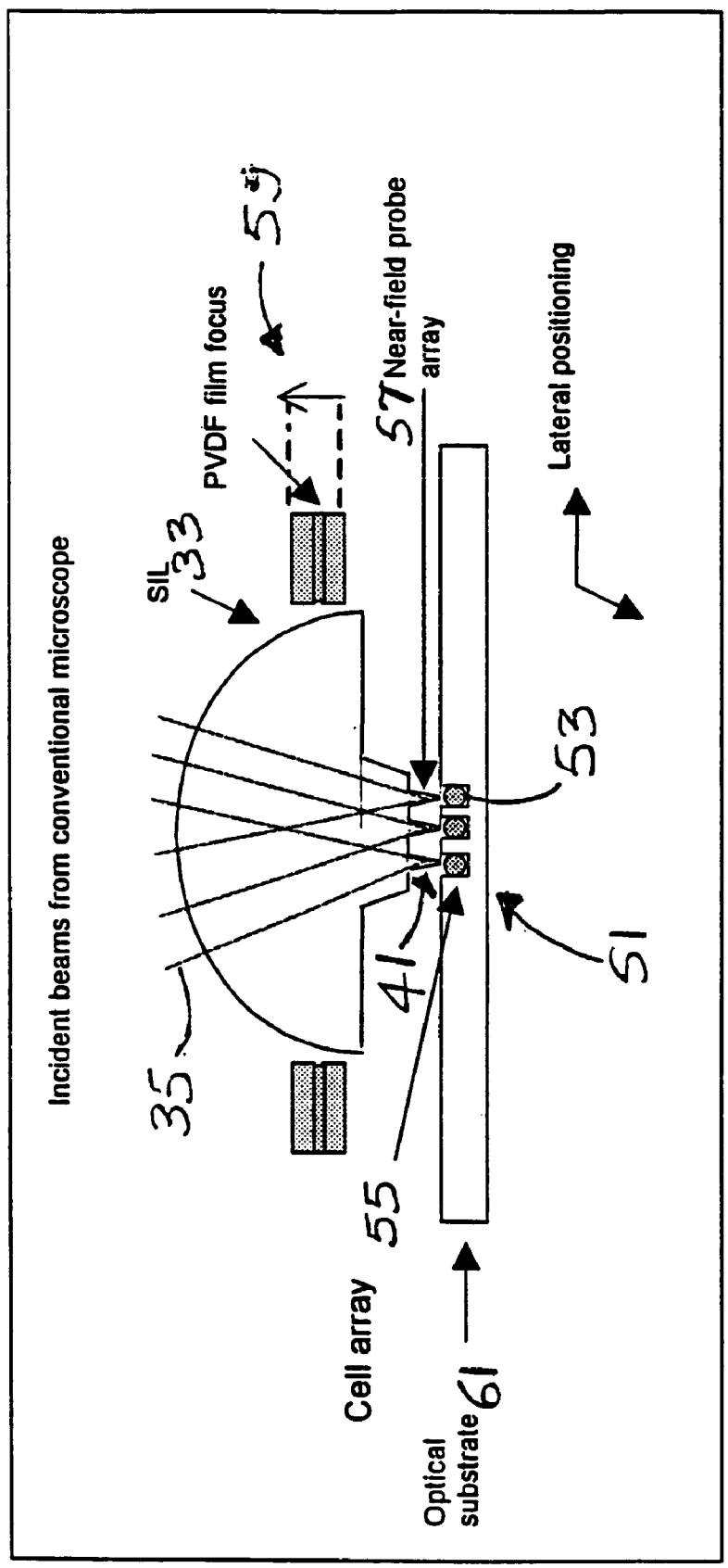
FIG. 9 shows the integrate POINT system including an array of near-field probes.

FIG. 9 shows the integrate POINT system including a probe array 57 of near-field probes 41 for intra-cellular imaging with sub-wavelength resolution imaging and spectroscopy 59 coupled with a precision focus control device and cell containment system 51.

Because of the unique configuration of the POINT system, direct viewing of cells and other biological material is possible. This is not the case with commercially available near-field scanning optical microscopes (NSOM). Until now, near-field probes were designed to move over the surface of the object being measured. The present invention uniquely provides a technique to penetrate the cell membrane with a near-field probe and to image the inside of an intact cell without destroying the cell structure. The POINT platform has many applications, including but not limited to, biomedical imaging, surface metrology and chemistry at the nanoscale.

The POINT invention, described in co-pending patent application Ser. No. 10/290,528, is incorporated herein by reference in its entirety. The POINT system encompasses an array of near-field probes which may consist of either an array of fiber probes or an array of probes formed at the base of a solid immersion lens for biological imaging which provides greater light throughput. POINT has the capability of simultaneously collecting image data and spectroscopy information in the vicinity of the near-field probes by combining multiple techniques such as fluorescence, Raman, and absorption spectroscopy. Producing a beam diameter only nanometers in size enables spectroscopy to be performed in a very small cross-section. There is an increase in optical efficiency when coupling light through a sub-wavelength aperture using a solid immersion lens.

Forming many probes in an array essentially provides a multiple aperture near-field microscope. This creates a means of analyzing multiple cells at once or multiple image points within a sample. The probe array combined with the cell tray, which contains a number of cells or other samples in a regular array of "buckets," provides a unique tool for cell analysis.

Using lithography techniques, the near-field microscope is fashioned with an array of probes with precisely the same period in two-dimensions as the cell tray. Multiple cells are then analyzed in an ordered fashion. The invention allows for efficient monitoring of cell activity including, but not limited to, response to drugs, protein content, gene expression, and the like, and enables each cell to be treated differently. The probe array may be built into a computerized stage for certain automated functions. Each cell well of interest can be precisely aligned to the near-field probe array.

This new probe works very well for cell penetration, which is applied as an array of near-field probes in an optical substrate. The geometry of the probe is easily determined from a series of cell poking experiments and light through-put measurements.

While the invention has been described with reference to specific embodiments, modifications and variations of the invention may be constructed without departing from the scope of the invention, which is defined in the following claims.

I claim:

1. A cell containment apparatus comprising a cell tray comprising a substrate, a multi-dimensional array of apertures on the substrate, a medium disposed in the apertures for monitoring, analyzing and processing of properties of the medium, wherein the apertures are cell wells receiving the medium to be analyzed, further comprising a probe disposed proximal the substrate for simultaneous monitoring, analysis and processing of the medium in each cell well, wherein the probe is an array of probes for parallel processing of the medium in each of the cell wells, wherein the probe is a precision optical intracellular near field imaging spectroscope, wherein the spectroscope comprises a nanosensor array of probes for non-invasively imaging sub-cellular and molecular inner regions of the medium being analyzed without destruction of the medium.

2. The apparatus of claim 1, wherein each cell well is disposed equidistant from an adjacent cell well in an orthogonal direction.

3. The apparatus of claim 1, wherein the array is a linear array or two-dimensional array.

4. The apparatus of claim 1, wherein the medium is a life support medium.

5. The apparatus of claim 1, wherein the medium is a solid or fluid sample.

6. The apparatus of claim 1, wherein the medium is selected from a group consisting of matrix of cells, biological fluids, chemicals, solid analytes, and combinations thereof.

7. The apparatus of claim 1, wherein the nanosensor array of probes are near-field probes for intra-cellular sub-wavelength resolution imaging of the medium in the cell wells.

8. The apparatus of claim 1, wherein the array of probes have spacings between the probes similar to spacings between the cell wells.

9. The apparatus of claim 8, wherein one probe of each of the array of probes monitors, processes and analyzes the medium in one of the cell wells proximal the one probe, and wherein the array of probes parallelly monitor, process and analyze the medium in the cell wells as desired.

10. The apparatus of claim 1, wherein the substrate comprises material having optimal transmission properties in all regions of an electromagnetic spectrum.

11. The apparatus of claim 1, wherein the substrate is an optical substrate.

12. The apparatus of claim 11, wherein the material of the optical substrate is selected from the group consisting of fused silica, soda lime glass, borosilicate glass, PMMA, sapphire, silicon, germanium, and combinations thereof.

13. The apparatus of claim 1, wherein the substrate comprises a photoresist coating.

14. The apparatus of claim 1, wherein the cell wells have different well depths on the substrate.

15. The apparatus of claim 1, further comprising optic lenses disposed at bottoms of each of the cell wells.

16. The apparatus of claim 15, wherein the optic lenses are micro-machined diffractive optic lenses.

17. The apparatus of claim 15, wherein the optic lenses are Fresnel lenses.

18. The apparatus of claim 1, wherein the substrate is a uniform flat surface.

19. The apparatus of claim 18, wherein the substrate is a microscope slide or a cover slip.

20. The apparatus of claim 19, wherein the substrate is an invar backing plate comprising clear apertures for viewing transmission.

21. The apparatus of claim 1, wherein the cell wells are micro-channels etched into the substrate for delivering the medium to each cell well.

22. The apparatus of claim 21, further comprising a delivery manifold, substances in the manifold, and fluid channels on the substrate connecting the manifold and the cells wells for delivering the substances to the cell wells.

23. The apparatus of claim 22, wherein the substances are selected from the group consisting of drugs, chemicals, dyes, fluids, and combinations thereof.

24. The apparatus of claim 1, wherein the cell tray is a square ordered array of cells.

25. A cell containment apparatus comprising a cell tray comprising a substrate, a multi-dimensional array of apertures on the substrate, a medium disposed in the apertures for monitoring, analyzing and processing of properties of the medium, wherein the substrate comprises a photoresist coating, further comprising a crossed-grating pattern of Ronchi-grating on the photoresist coating.

26. The apparatus of claim 25, further comprising a lithographic shadow mask forming the apertures on the photoresist coating.

27. A cell containment apparatus comprising a cell tray comprising a substrate, a multi-dimensional array of apertures on the substrate, a medium disposed in the apertures for monitoring, analyzing and processing of properties of the medium, wherein the substrate comprises a photoresist coating, further comprising a crossed-grating interference pattern on the photoresist coating formed by holographic exposure.

28. A cell containment apparatus comprising a cell tray comprising a substrate, a multi-dimensional array of apertures on the substrate, a medium disposed in the apertures for monitoring analyzing and processing of properties of the medium, wherein the apertures are cell wells receiving the medium to be analyzed, further comprising a probe disposed proximal the substrate for simultaneous monitoring, analysis and processing of the medium in each cell well, wherein the probe is an array of probes for parallel processing of the medium in each of the cell wells, wherein the probe is a precision optical intracellular near field imaging spectroscope, wherein the spectroscope comprises a nanosensor array of probes for non-invasively imaging sub-cellular and molecular inner regions of the medium being analyzed without destruction of the medium, wherein the substrate comprises a photoresist coating, and further comprising a two-dimensional ordered array of shaped regions formed on the photoresist coating.

29. The apparatus of claim 28, wherein the shaped regions have geometric shapes selected from the group consisting of circles, triangles, squares, rectangles, rhombus, pentagons, hexagons, octagons, and combinations thereof.

30. A cell containment apparatus comprising a cell tray comprising a substrate, a multi-dimensional array of apertures on the substrate, a medium disposed in the apertures for monitoring, analyzing and processing of properties of the medium, wherein the substrate comprises a photoresist coating, further comprising an intermediate layer between the substrate and the photoresist coating.

31. A method for analyzing a medium comprising providing the medium in a multi-dimensional array of cell wells on a substrate of a cell tray in a cell containment apparatus, and simultaneously monitoring, analyzing and processing the medium and determining properties of the medium, further comprising disposing a probe proximal the substrate for the simultaneous monitoring, analyzing and processing of the medium in each cell well, wherein the disposing the probe comprises disposing an array of probes and parallelly processing the medium in each of the cell wells, wherein the parallelly processing comprises imaging the medium with a precision optical intracellular near field imaging spectroscope, wherein the imaging comprises non-invasively imaging sub-cellular and molecular inner regions of the medium with a nanosensor array of probes without destroying the medium.

32. The method of claim 31, wherein the providing the medium comprises providing a life support medium.

33. The method of claim 32, wherein the providing the life support medium comprises providing a solid or fluid sample.

34. The method of claim 31, wherein the providing the medium comprises providing the medium selected from the group consisting of matrix of cells, biological fluids, chemicals, solid analytes, and combinations thereof.

35. The method of claim 31, wherein the imaging with the nanosensor array of probes comprises imaging intra-cellular sub-wavelength resolution of the medium in the cell wells with the near-field probes.

36. The method of claim 35, wherein the imaging with the probes comprises imaging the medium in one of the cell wells with one probe of each of the array of probes proximal the one cell well, and parallelly monitoring, processing and analyzing the medium in the cell wells with the array of probes.

37. The method of claim 31, further comprising imaging the medium with optic lenses disposed at bottoms of each of the cell wells.

38. The method of claim 37, wherein the imaging with the optic lenses comprises micro-machining diffractive optic lenses at the bottoms of each of the cell wells for optical transmission and processing of the medium in each of the cell wells with a spectroscope or a microscope.

39. A process for fabricating a cell containment device comprising forming a cell tray with a substrate, forming an array of cell wells on the substrate, providing a medium of interest in the cell wells, and imaging the medium in the cell wells, wherein the forming the cell tray with the substrate comprises forming a substrate with optimal optical transmission properties in all regions of an electromagnetic spectrum, wherein the forming the cell tray with the substrate comprises coating the substrate with a photoresist layer, wherein the forming the cell wells comprises exposing a crossed-grating pan em with a Ronchi-grating on the photoresist coating.

40. The process of claim 39, wherein the forming the cell tray with the substrate comprises forming a substrate with material selected from the group consisting of fused silica, soda lime glass, borosilicate glass, PMMA, sapphire, silicon, germanium, and combinations thereof.

41. The process of claim 39, wherein the forming the cell wells comprises masking with a lithographic shadow on the photoresist coating.

42. The process of claim 39, further comprising imaging the medium of interest with a probe.

43. The process of claim 42, wherein the imaging with the probe comprises fabricating an array of probes with spacing identical to spacing between the cell wells, parallelly and simultaneously processing, monitoring, and analyzing the medium of interest in the cell wells.

44. The process of claim 39, wherein the imaging comprises integrating the cell tray with a microscope objective lens array, disposing the lens array above a sample of interest, and processing and analyzing the sample of interest.

45. The process of claim 39, wherein the forming the cell tray with the substrate comprises mounting the cell tray onto an invar backing plate with a clear aperture for viewing transmission.

46. The process of claim 45, wherein the mounting the cell tray comprises forming a mechanical support and maintaining a uniform flat surface of the cell tray.

47. The process of claim 39, wherein the forming the cell tray comprises machining the cell tray into microscope slides or cover slips or optical substrates.

48. The process of claim 39, wherein the forming the cell tray with the substrate comprises etching an integrated network of micro-channels into the substrate, and providing medium delivery to each cell well.

49. The process of claim 48, wherein the etching comprises forming the network as flow channels on the substrate using photolithography transfer process or shadow mask, dedicating a delivery channel to each cell well, and extending the channel from each cell well to an edge of the substrate.

50. The process of claim 49, further comprising coupling a delivery manifold to the substrate, communicating the delivery channels of the cell wells with the manifold, providing substances in the delivery manifold, and supplying the substances from the delivery manifold via the delivery channels to the cell wells.

51. The process of claim 50, wherein the supplying the substances comprises supplying substances selected from the group consisting of drugs, chemicals of different concentrations, chemicals of different pH, dyes, and combinations thereof.

52. A process for fabricating a cell containment device comprising forming a cell tray with a substrate, forming an array of cell wells on the substrate, providing a medium of interest in the cell wells, and imaging the medium in the cell wells, wherein the forming the cell tray with the substrate comprises forming a substrate with optimal optical transmission properties in all regions of an electromagnetic spectrum, wherein the forming the cell tray with the substrate comprises coating the substrate with a photoresist layer, wherein the forming the cell wells comprises holographically exposing a crossed-grating interference pattern on the photoresist coating.

53. The process of claim 52, wherein the forming the cell tray with the substrate comprises exposing the photoresist layer with laser light or broadband white light.

54. The process of claim 52, wherein the forming the cell tray with the substrate comprises forming a substrate with material selected from the group consisting of soda lime glass, borosilicate glass, fused silica, PMMA, sapphire, silicon, germanium, and combinations thereof.

55. The process of claim 52, wherein the imaging comprises incorporating a diffractive optic lens at bases of each cell well, microscopically imaging and analyzing the medium of interest using solid and liquid immersion optical techniques for high-resolution imaging.

56. The process of claim 55, wherein the incorporating comprises micro-machining the diffractive optic lens as an integrated part of the cell tray during the micro-machining to generate the cell wells.

57. The process of claim 56, wherein the incorporating comprises forming a fresnel-type lens structure at the base of each well with a binary transmittance or grayscale mask, and a phase mask or kinoform.

58. The process of claim 52, further comprising indexing each cell well with an automation system, and monitoring and processing the medium of interest.

59. The process of claim 58, wherein the imaging comprises simultaneous collection of light for imaging by the indexed cell wells and spectroscopy analysis of the medium of interest in multiple regions of an electromagnetic spectrum.

60. The process of claim 59, wherein the imaging comprises using the cell tray in transmission or reflection mode microscopes and spectrometer configurations in ultraviolet, visible and infrared regions of the electromagnetic spectrum.

61. The process of claim 52, wherein the forming the cell tray with the substrate comprises forming an integrated micro-optic chip on an optical wafer substrate for parallel processing and analysis of a large number of cell wells, and regulating and precisely delivering substances to each cell well.

62. The process of claim 52, further comprising integrating an array of probes with the cell tray, and simultaneously imaging and analyzing the cell wells with the array of probes.

63. A process for fabricating a cell containment device comprising forming a cell tray with a substrate, forming a multi-dimensional array of apertures on the substrate, disposing a medium in the apertures for monitoring, analyzing and processing of properties of the medium, wherein the forming the apertures includes forming cell wells receiving the medium to be analyzed, disposing a probe proximal the substrate for simultaneous monitoring, analysis and processing of the medium in each cell well, wherein the disposing a probe includes disposing an array of probes for parallel processing of the medium in each of the cell wells wherein the disposing robe further includes disposing a precision optical intracellular near field imaging spectroscope, wherein the spectroscope comprises a nanosensor array of probes for non-invasively imaging sub-cellular and molecular inner regions of the medium being analyzed without destruction of the medium, wherein the forming the cell tray with a substrate comprises coating the substrate with a photoresist coating, and wherein the forming the cell wells comprises forming a two-dimensional ordered array of shaped regions on the photoresist coating.

64. The process of claim 63, wherein the forming the shaped regions comprises forming regions with geometric shapes selected from the group consisting of circles, triangles, squares, rectangles, rhombus, pentagons, hexagons, octagons, and combinations thereof.

65. A process for fabricating a cell containment device comprising forming a cell tray with a substrate, forming a multi-dimensional array of apertures on the substrate, disposing a medium in the apertures for monitoring, analyzing and processing of properties of the medium, wherein the forming the apertures includes forming cell wells receiving the medium to be analyzed, disposing a probe proximal the substrate for simultaneous monitoring, analysis and processing of the medium in each cell well, wherein the disposing a probe includes disposing an array of probes for parallel processing of the medium in each of the cell wells, wherein the disposing a probe further includes disposing a precision optical intracellular near field imaging spectroscope, wherein the spectroscope comprises a nanosensor array of probes for non-invasively imaging sub-cellular and molecular inner regions of the medium being analyzed without destruction of the medium, wherein the forming the cell tray with a substrate comprises coating the substrate with a photoresist coating, wherein the forming the cell tray with the substrate further comprises exposing the photoresist layer with laser light or broadband white light, further comprising after developing the substrate, retaining unexposed portions on the photoresist layer as surface structures, and forming a two-dimensional ordered array of geometrically shaped regions on the substrate.

66. The process of claim 65, wherein the exposing the photoresist layer comprises exposing with negative or positive photoresist processes.

67. The process of claim 66, wherein the exposing the photoresist layer comprises substituting the positive photoresist process with a negative of an aperture mask.

68. The process of claim 65, wherein the forming the cell wells comprises forming the cell wells with e-beam or deep UV lithography on the substrate.

69. The process of claim 68, further comprising processing photoresist patterns on the substrate with reactive ion etching procedure, differentially etching the substrate and the photoresist layer, and etching features into the substrate deeper than a thickness of the photoresist layer.

70. The process of claim 69, wherein the differentially etching the substrate comprises forming various well depths of the cell wells.

71. The process of claim 69, wherein the differentially etching comprises etching with a fluorine based chemical etchant.

72. A process for fabricating a cell containment device comprising forming a cell tray with a substrate, forming an array of cell wells on the substrate, providing a medium of interest in the cell wells, and imaging the medium in the cell wells, wherein the forming the cell tray with the substrate comprises forming a substrate with material selected from the group consisting of soda lime glass, borosilicate glass, fused silica, PMMA, sapphire, silicon, germanium, and combinations thereof, further comprising processing photoresist patterns on the substrate with reactive ion etching procedure, differentially etching the substrate and the photoresist layer, and etching features into the substrate deeper than a thickness of the photoresist layer, wherein the differentially etching comprises etching with a fluorine based chemical etchant, further comprising forming deeper cell wells by disposing an intermediate layer between the substrate and the photoresist layer.

73. The process of claim 72, wherein the disposing the intermediate layer comprises depositing art aluminum layer impervious to the fluorine based chemical etchant, removing the metallic layer, and etching the deeper cell wells in the substrate.

74. A process for fabricating a cell containment device comprising forming a cell tray with a substrate, forming an array of cell wells on the substrate, providing a medium of interest in the cell wells, and imaging the medium in the cell wells, further comprising integrating an array of probes with the cell tray, and simultaneously imaging and analyzing the cell wells with the array of probes, wherein the integrating comprises integrating near-field probes at bases of the lenses in the cell wells, imaging intra-cellular-structure in the medium of interest with sub-wavelength resolution imaging and spectroscopy, coupling the integrated probe and the cell tray to a precision focus control device, and directly viewing inside the medium of interest by non-invasively penetrating a membrane on the medium of interest, and imaging insides of an intact medium without destroying the structure.

75. The process of claim 74, wherein the imaging insides comprises bio-medical imaging, surface metrology and nanoscale chemistry of the medium of interest.

* * * * *

UNITED STATES PATENT AND TRADEMARK OFFICE
CERTIFICATE OF CORRECTION

PATENT NO. : 7,190,449 B2 Page 1 of 1
APPLICATION NO. : 10/693953
DATED : March 13, 2007
INVENTOR(S) : Daniel G. O'Connell It is certified that error appears in the above-identified patent and that said Letters Patent is hereby corrected as shown below:

Column 4, Line 2: Delete word "lens" at beginning of line.

Column 4, Line 25: Delete word "camber" and substitute word --chamber--.

Column 10, Line 38: In Claim 63, delete word "robe" and substitute word --probe--.

Signed and Sealed this

Thirtieth Day of September, 2008

JON W. DUDAS
*Director of the United States Patent and Trademark Office*